(12) United States Patent
Scherer et al.

(10) Patent No.: US 10,172,520 B2
(45) Date of Patent: Jan. 8, 2019

(54) MINIMALLY INVASIVE WIRELESS SENSING DEVICES AND METHODS

(71) Applicant: CALIFORNIA INSTITUTE OF TECHNOLOGY, Pasadena, CA (US)

(72) Inventors: Axel Scherer, Barnard, VT (US); Muhammad Mujeeb-U-Rahman, San Gabriel, CA (US); Meisam Honavar Nazari, Pasadena, CA (US); Muhammad Musab Jilani, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 160 days.

(21) Appl. No.: 15/222,866

(22) Filed: Jul. 28, 2016

(65) Prior Publication Data

US 2017/0055835 A1 Mar. 2, 2017

Related U.S. Application Data

(60) Provisional application No. 62/208,960, filed on Aug. 24, 2015, provisional application No. 62/212,196, filed on Aug. 31, 2015, provisional application No. 62/246,516, filed on Oct. 26, 2015.

(51) Int. Cl.
*A61B 5/00* (2006.01)
*A61B 5/145* (2006.01)
*G06F 19/00* (2018.01)
*G16H 40/67* (2018.01)
*A61B 5/1473* (2006.01)
*A61B 5/1459* (2006.01)

(52) U.S. Cl.
CPC ........ *A61B 5/0022* (2013.01); *A61B 5/14521* (2013.01); *A61B 5/685* (2013.01); *G06F 19/00* (2013.01); *G16H 40/67* (2018.01); *A61B 5/1459* (2013.01); *A61B 5/1473* (2013.01); *A61B 5/14532* (2013.01); *A61B 5/14539* (2013.01); *A61B 5/6832* (2013.01); *A61B 2560/0214* (2013.01); *A61B 2562/12* (2013.01)

(58) Field of Classification Search
CPC ..... A61B 5/0022; A61B 5/685; A61B 5/1459; A61B 5/14532; A61M 37/0015; A61M 2037/0023
See application file for complete search history.

(56) References Cited

U.S. PATENT DOCUMENTS

| | | | | |
|---|---|---|---|---|
| 8,947,656 | B2* | 2/2015 | Cunningham | G01J 3/44 356/300 |
| 2005/0035309 | A1* | 2/2005 | Bobrov | F41J 2/02 250/504 R |
| 2006/0211933 | A1* | 9/2006 | Zimmermann | A61B 5/14514 600/352 |
| 2008/0015494 | A1* | 1/2008 | Santini, Jr. | A61M 5/1409 604/65 |
| 2013/0303865 | A1* | 11/2013 | Rebec | A61B 5/0082 600/310 |

\* cited by examiner

*Primary Examiner* — Bradley J Osinski
(74) *Attorney, Agent, or Firm* — Steinfl + Bruno LLP (57) ABSTRACT

A sensing device allows detection of biological quantities in ways that are minimally invasive. Micrometer or nanometer sized needles allow sensing of bodily fluids in a minimally invasive method. The device comprises electronics and power harvesting. Antennas or coils allow communication and power harvesting from an external device, which can be attached to smartphones to allow operation of a camera and camera light for biosensing.

15 Claims, 12 Drawing Sheets

MINIMALLY INVASIVE WIRELESS SENSING DEVICES AND METHODS

CROSS REFERENCE TO RELATED APPLICATIONS

The present application claims priority to U.S. Provisional Patent Application No. 62/208,960, filed on Aug. 24, 2015, U.S. Provisional Patent Application No. 62/212,196, filed on Aug. 31, 2015, and U.S. Provisional Patent Application No. 62/246,516, filed on Oct. 26, 2015, the disclosures of all of which are incorporated herein by reference in their entirety.

TECHNICAL FIELD

The present disclosure relates to biosensing. More particularly, it relates to minimally invasive wireless sensing devices and methods.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, a device is described, the device comprising a substrate; a container on a top surface of the substrate; and a plurality of needles on a bottom surface of the substrate, the plurality of needle connected to the container and configured to allow a fluid flow between needle tips and the container.

In a second aspect of the disclosure, a system is described, the system comprising a sensing device comprising: a substrate; a container on a top surface of the substrate; a plurality of needles on a bottom surface of the substrate, the plurality of needle connected to the container and configured to allow a fluid flow from needle tips to the container; at least one sensor on the substrate, the at least one sensor configured to analyze the fluid in the container; and an antenna or coil on the substrate; and an external reader device, configured to communicate with the sensing device trough the antenna or coil.

In a third aspect of the disclosure, a system is described, the system comprising a sensing device comprising: a substrate; a container on a top surface of the substrate; a plurality of needles on a bottom surface of the substrate, the plurality of needles connected to the container and configured to allow a fluid flow from needle tips to the container; at least one sensor on the substrate, the at least one sensor configured to analyze the fluid in the container; and an antenna or coil on the substrate; and a snap-on accessory, configured to attach on an external reader device, wherein: the external reader device comprises a camera and a camera light and is configured to communicate with the sensing device trough the antenna or coil, and the snap-on accessory comprises filters, the filters configured to filter electromagnetic radiation from the camera light to the sensing device and from the sensing device to the camera.

The above mentioned aspects are presented in way of example and not of limitation.

DETAILED DESCRIPTION

Minimally invasive sensing systems lie between the fully invasive implantable and non-invasive wearable systems. These systems sense signals by accessing the required signal with a minimally invasive method. For example, access to interstitial fluid can be made by different methods including applying small voltages across the skin, which cases some fluid to permeate out through pores. Another method can be to create small holes in the skin and access the fluids through the holes.

Wearable sensors are limited in the type of signals that can be acquired. Fully implantable systems, on the other hand, need very careful design and can still suffer from rejection responses from the host subject due to the inserted foreign body. Therefore, minimally invasive systems, as described in the present disclosure, can provide an advantageous solution compared to non invasive and fully invasive systems.

In some embodiments of the present disclosure, minimally invasive sensing systems comprise very small needles, which allow access to body fluids without rupturing blood vessels or affecting any major part of the skin. These needles create pores around themselves and provide very good seal on the outer surface of the needles, in contact with the skin. Both micrometer-sized and nanometer-sized needles can be used. For example, smaller needles can access interstitial fluid due to change in fluid pressures and through capillary action. For example, the introduction of the needle creates a change in pressure which draws the fluid outward, through the needle. Capillary action or an active pressure change caused by, for example, mechanical pumping can also be used.

In some embodiments, the fluid exchange can be blocked from occurring continuously, and instead be activated at a desired time, in order to access real-time information. In other embodiments, one-time samples can be useful for lab tests etc. In yet other embodiments, integrated sensors in contact with the fluid can be advantageous and provide adequate continuous sensing.

The systems described herein can be used for closed loop drug delivery, for example. The reservoirs can be filled from the outside or even replaced without changing the rest of the system. By using very small needles (such as nanoneedles) it is possible to stop the cells from sealing the needle opening, which can allow use of the needles for a longer duration compared to larger needles. Micro needles can be fabricated with dimensions smaller than most biological cells. Surface processing of the needles can help in minimizing biofouling and scar tissue formation. The small size of the needles can also help minimize damage to local tissues. The needles can be made with flexible materials to further minimize damage due to the motion of needle relative to the tissue. Electronic control can help clean the needle surfaces and openings to lengthen the usability of the system.

In some embodiments, minimally invasive sensing can be carried out with a complementary metal-oxide semiconductor (CMOS) sensor on a device which can be attached like a skin-patch, with a wireless operation mode. The skin patch is used to keep the sensor close to the skin to access, for example, sweat. A small needle patch or similar device (e.g. thermal heater) can be used to increase the fluid availability near the sensor. The sensor can be wirelessly communicating with a reader device to transmit information and data. This system can be used for measuring constituents of sweat or other environment and bodily fluids.

Figure 1:
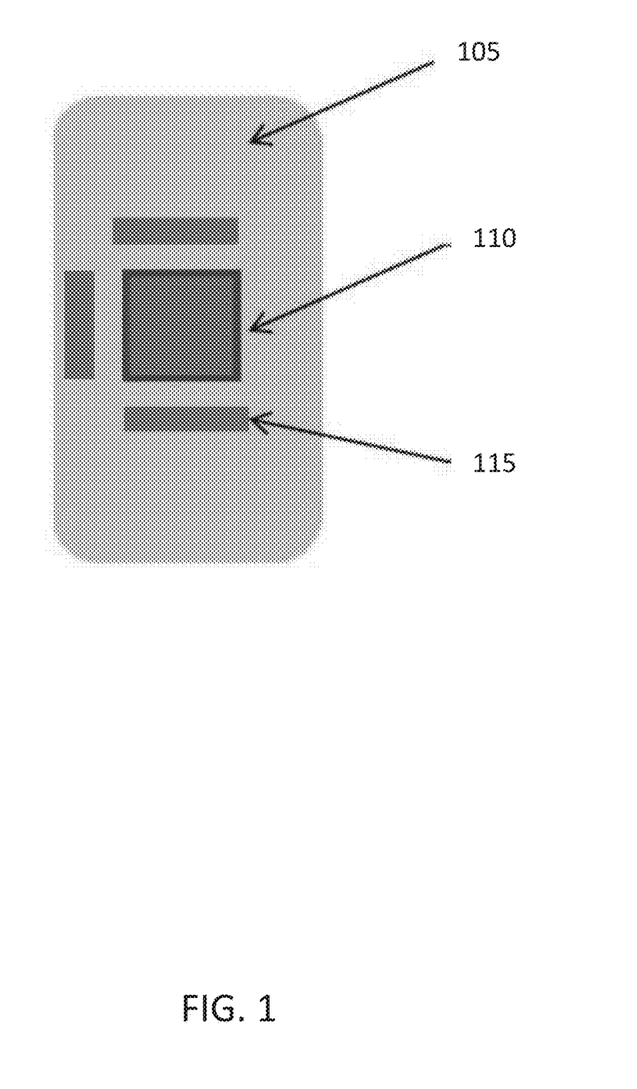
FIG. 1 illustrates minimally invasive sensing using a skin patch and a wireless sensor.

As visible in FIG. 1, a sensing system can comprise a skin patch (105), a wireless sensing platform (110) and needle assemblies (115).

In other embodiments, another system design comprises of a top fluid container which houses the fluid for sensing and also allows flowing of the fluid around the system for proper operation of the system. In embodiments for drug delivery, there can be multiple subcontainers to deliver drugs in a controlled manner. For example, the subcontainers could be within the top container. The fluid container can have multiple layers for environment protection and usability. An electronic control system controls system operation using some ASIC or programmable devices and other system components. An actuation system is responsible for generating actuation signals and actual physical actuation, if needed.

Figure 2:
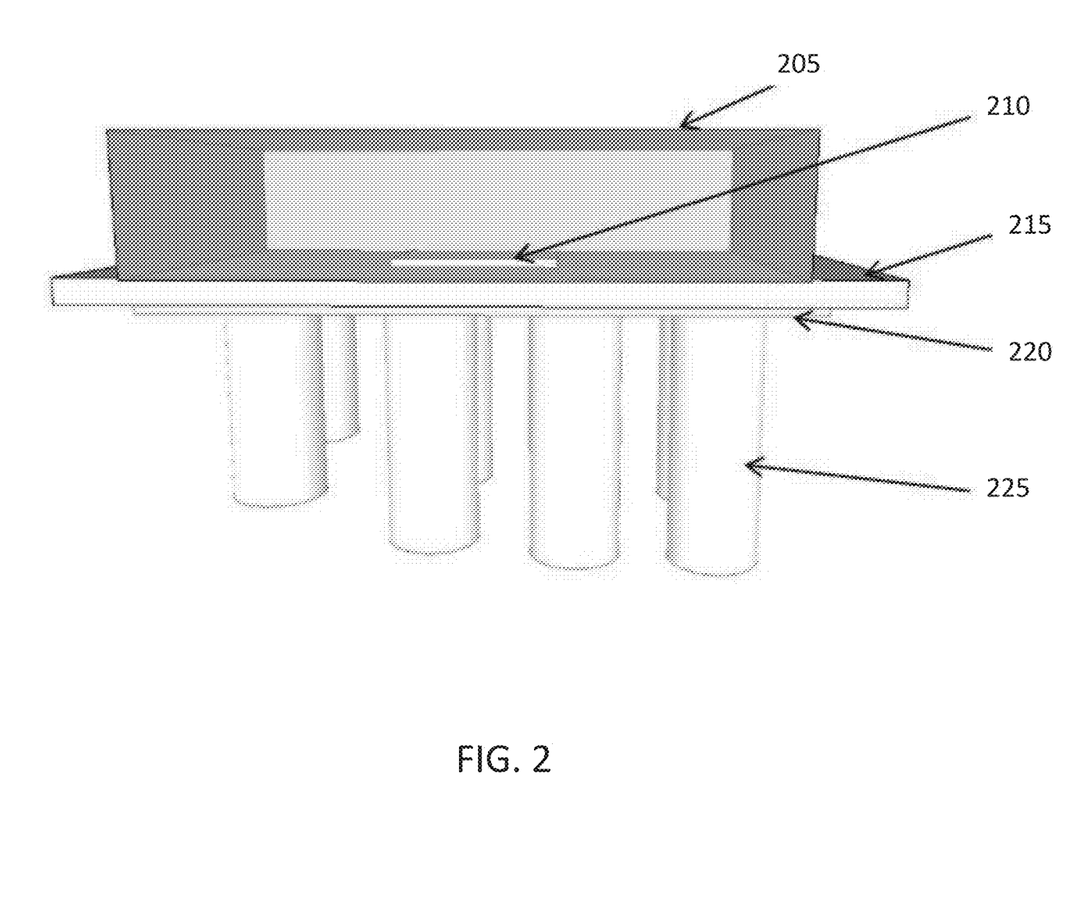
FIG. 2 illustrates a PCB with components on both sides.

As visible in FIG. 1, a sensing system can comprise a fluid container (205), an integrated circuit (210), an electronic control system (215), an actuation system (220) and micro or nano needles (225). This system can be fabricated on a printed circuit board (PCB).

The systems described herein can have different integrated components for different requirements. In some cases, the integrated system can be a completely wireless system with wireless powering and communication, coupled with an integrated or bonded sensor. In other cases, an integrated system can be an ASIC for controlling a sensor, but the powering and communication can be carried out through on-board batteries and wireless systems (e.g. Bluetooth™ or long distance RF). The systems can be designed to be modular. The part of the system which comprises needles can be fabricated as a single part, which can be replaced after the needles are blocked by the growth of proteins and other cells within the needles. Electrical or mechanical actuation or thermal heating can be used to clean the needles in certain embodiments. Pressure can be used to induce flow across the needles, if necessary.

The systems components for a particular application can be chosen based upon specific requirements and not all components are needed for all systems. For example, a simpler implementation could be just using the micro/nano needles, along with a liquid container and a platform capable of complete wireless operation as well as sensing. In a different configuration, some method of regenerating the fluid flow through the needles can be included once the biological entities (cells, proteins, etc.) seal the needles.

In some embodiments, the sensing system can be fabricated on a silicon-on-insulator (SOI) platform. A completely wireless sensing and actuation platform can be realized using this technology, gaining advantages for certain applications.

Different integrated technologies can be used to realize wireless integrated sensors. These sensors can be used to monitor different important parameters like metabolites, pH and gas pressures. Silicon-on-insulator and other similar technologies that allow fabrication of a device layer on an insulator possess inherent isolation between the different components. These systems can also be used to take advantage of the silicon-processing capabilities that have been acquired over time and which have resulted in enormous device manufacturing capabilities at low cost and high volume. The present disclosure describes details of such system implementations for the specific case of a system with simultaneous glucose and insulin sensing as it can provide a unique system capable for sensing in healthy and diabetic as well as prediabetic people. The person of ordinary skill in the art will understand that similar systems fabricated on insulators can be applied to other cases and not only for diabetes sensing.

Figure 3:
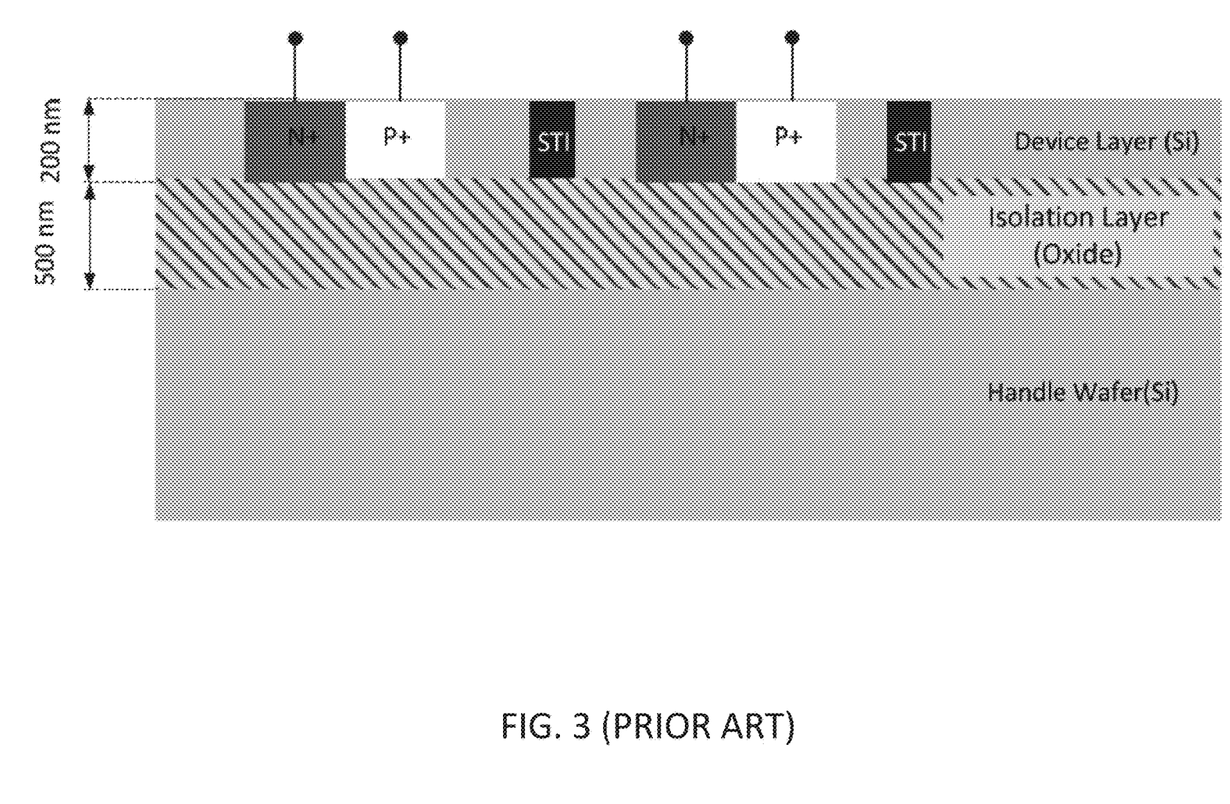
FIG. 3 depicts a CMOS electronic system.

A typical CMOS electronic system based on silicon-on-insulator is shown in FIG. 3. In FIG. 3, it is shown that trench isolation (e.g. STI) can be used to create isolation between different devices in this type of system. This can be very useful as one part of the die can be processed independently of the other. For example, high surface area electrodes can be fabricated and such isolations can be used to create electrically insulated electrodes as are needed for electrochemical sensors. This process can be carried out before a CMOS fabrication process and the electrodes can be coated with insulations, which can be removed after the rest of the CMOS process to expose the sensor parts again. Other methods can also be used to realize the above result.

SOI technologies with thick silicon layers can be useful for photo-absorption as well as for high surface area electrodes. In some cases, higher thickness can be traded off with low performance electronics as for most applications (e.g. biosensing), the performance requirements on electronics can be much more conservative.

The SOI systems can be used to realize integrated photovoltaic structures which are isolated from each other and hence generation of high voltages by cell stacking is more straightforward than in standard CMOS process. As the silicon layer is normally thin in such technologies, photo-absorption would be very low. However, some light-trapping methods can be used to further increase device efficiency. A simple method is using the top metal structures as bottom reflectors and using backside illumination. For this, the thick handling substrate on the back of the devices needs to be etched.

Figure 4:
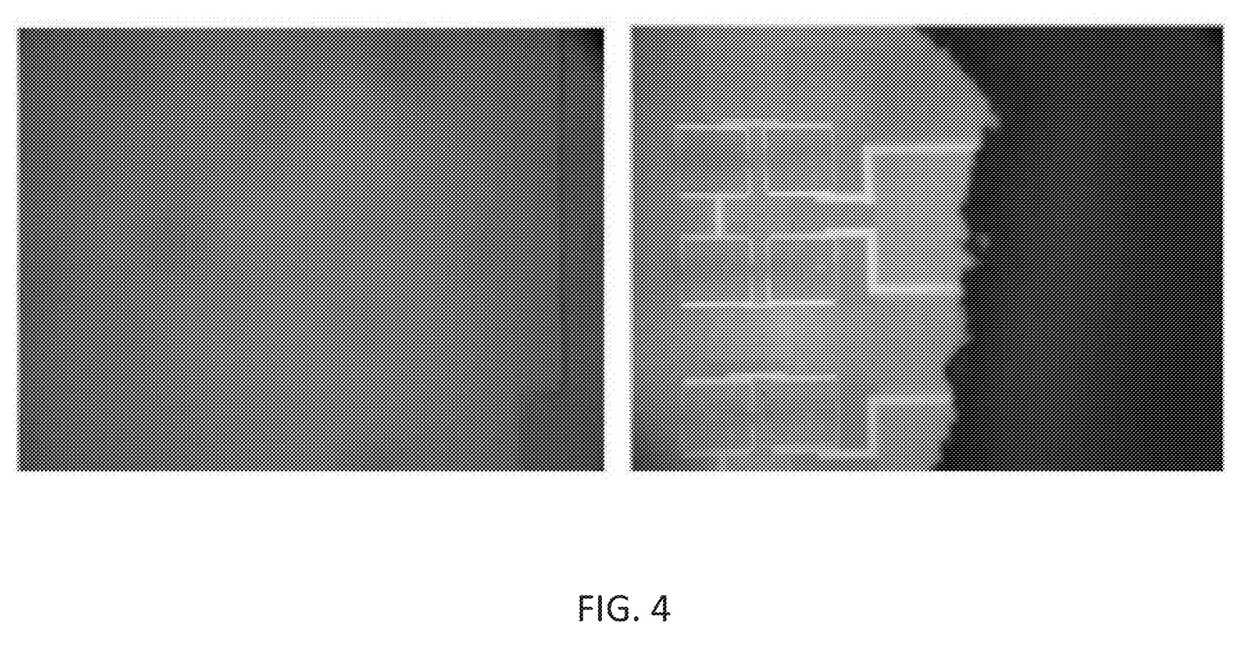
FIG. 4 illustrates SOI-CMOS structures after etching.

Etching was performed using aligned backside lithography and gas phase etching (using xenon difluoride). The silicon oxide insulation layer was used as an etch stop. The resulting structures are shown in FIG. 4.

Figure 5:
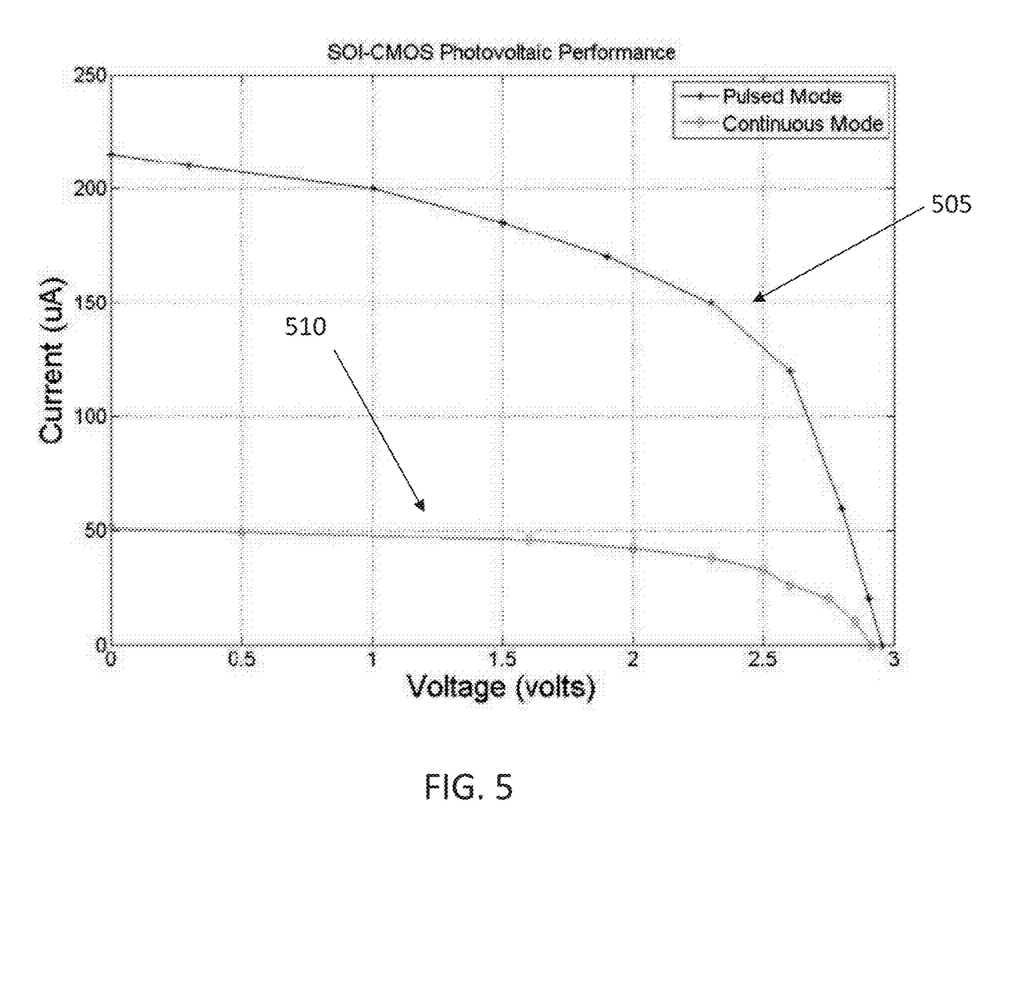
FIG. 5 illustrates photovoltaic measurements results using both continuous and pulsed mode.

The resulting structures can be backfilled with materials which can act as thermal heat sinks to keep the device layer cool during exposure of high optical fields. Also, the device is not normally powered constantly, and power pulsing can be used to avoid overheating of the device layer to avoid any damage. In FIG. 5, results of optical powering using both continuous (510) and pulsed mode (505) are shown.

The sensing systems can have multiple working electrodes which can share same counter electrodes and/or reference electrodes. Different chemistry on each electrode can be used to sense different components of the surrounding environment. In some cases, the electrode area is sufficient to allow each electrode of the system to be different from the other electrodes. The systems may have two or more electrodes.

Figure 6:
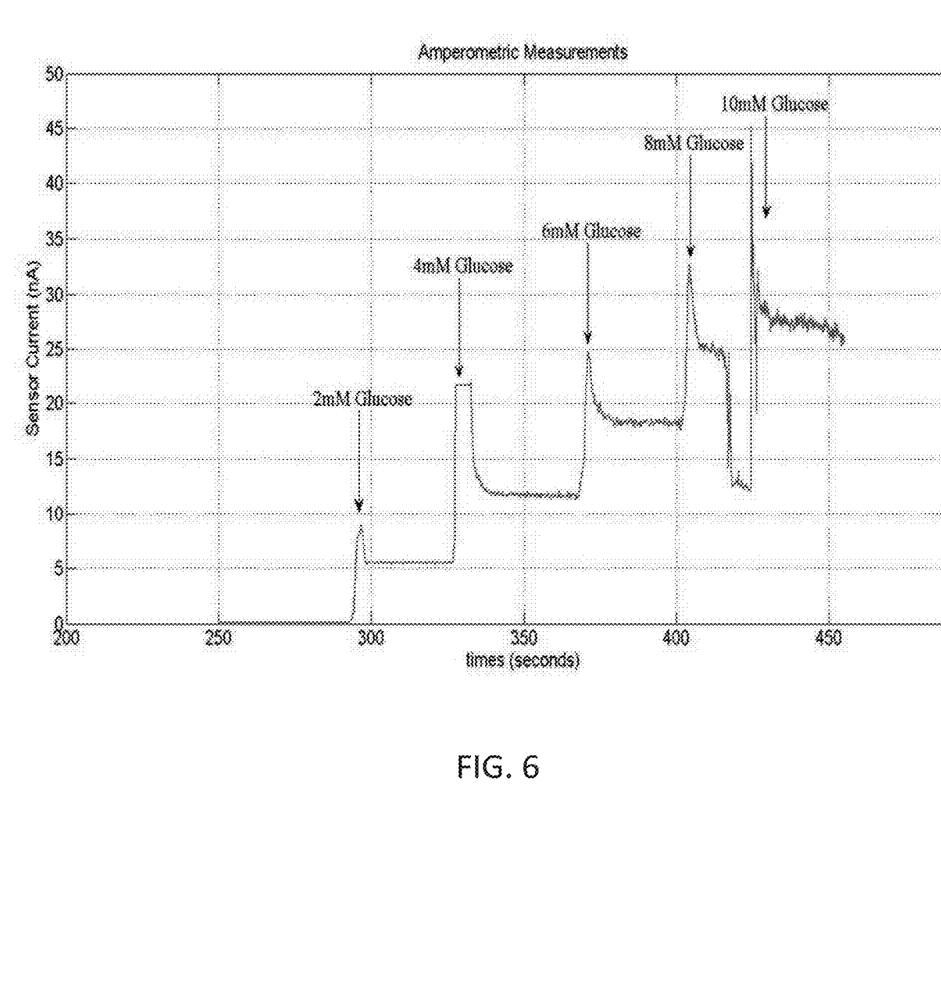
FIG. 6 illustrates amperometric glucose sensing using an integrated planar sensor.

In some embodiments, the systems can be used to detect different signals. For example, as described above, by using different electrodes for multiple sensing. An example of multiple sensing would be that of glucose and insulin. Glucose sensing can be carried out electrochemically using oxidoreductases enzymes, while insulin sensing can also be carried out electrochemically using insulin sensitive layers (e.g. insulin sensitive aptamers) along with some optional redox probe or some other method of creating change in the electrochemical signature in the presence of glucose. Some exemplary results of glucose and insulin sensing are shown in FIGS. 6 and 7.

Figure 7:
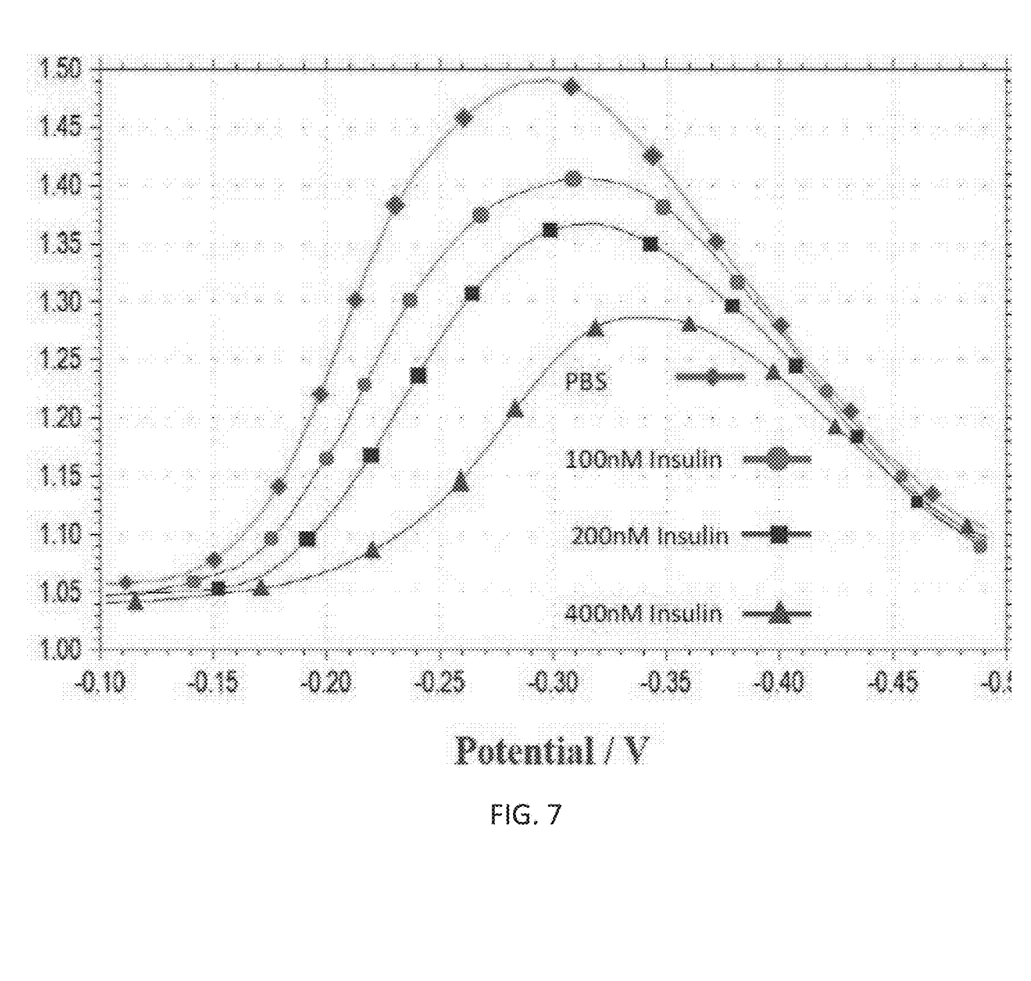
FIG. 7 illustrates electrochemical insulin detection using aptamers.

In FIG. 7, different curves are graphed for: PBS (705); 100 nM insulin (710); 200 nM insulin (715); and 400 nM insulin (720).

SOI technologies can achieve high reliability in electronic processing circuitry. The same circuits can be used to sense multiple electrodes based upon external commands or using internal switching. Additionally, the sensing parameters can be sent externally or pre-programmed in the system.

In some embodiments, integrated metallic structures (coils, antennas) can be used to communicate with an external receiver. These structures can also be used to receive power and command signals from external devices. Since photovoltaic structures can be shaped in many ways, the final system shape can be optimized for the required application. The shape depends upon the requirements of the application. Back side silicon can be etched with trenches followed by front side silicon etching and HF release of silicon oxide. In some other cases, laser cutting can be used to fabricate this structure. An example of a sensing system with different components is shown in FIG. 8.

Figure 8:
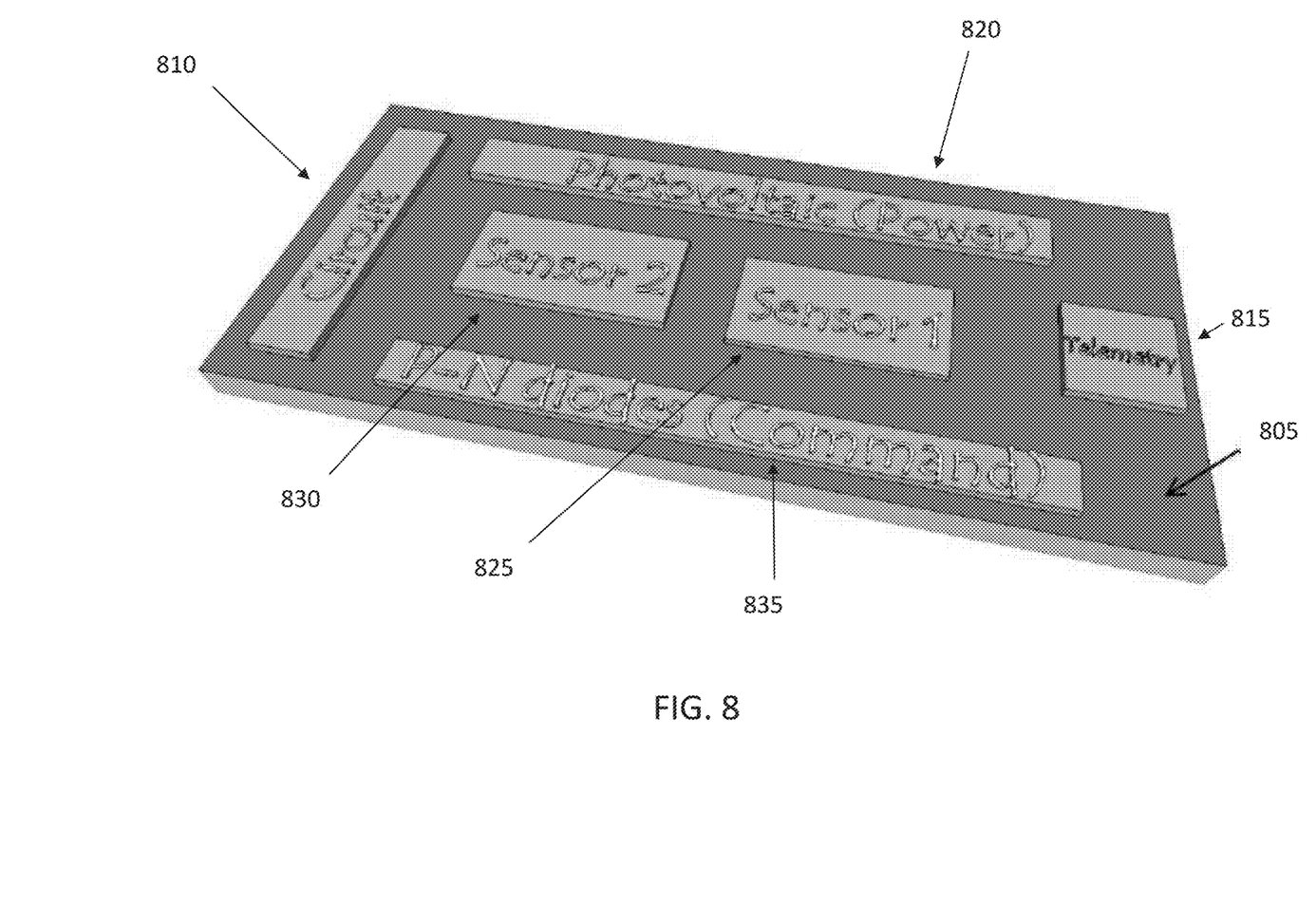
FIG. 8 illustrates an exemplary sensing system.

In FIG. 8, different components are illustrated on a SOI substrate (805): electronic circuits (810), photovoltaic cells for power generation (820), a telemetry module (815), a first sensor (825) and a second sensor (830), and p-n diodes for controlling other modules (835).

Wireless sensor technology can be advantageous to employ in the systems described in the present disclosure, for sensing in medical and biological applications. In some embodiments, wireless technology can be employed to wirelessly connect a sensing system to a reader device, for communication and power provision, or both. The reader can power up the wireless system, send and receive data to/from it, and also find its location precisely.

The actual reader design can vary depending on the design of the sensor and the environment in which the sensor is being used. For electromagnetically powered systems, the readers need to generate RF signals of the desired properties (frequency, modulation) to power up the chip as well as to communicate with it (e.g. to send commands). A robust and programmable sensor can make the entire system more practical.

A wireless reader for the sensing systems of the present disclosure can be a device for generating RF signals and for receiving the backscattered data from the sensing system. A small and low cost reader can be fabricated with commercially available integrated circuits. An exemplary block diagram of a reader system is shown in FIG. 9.

Figure 9:
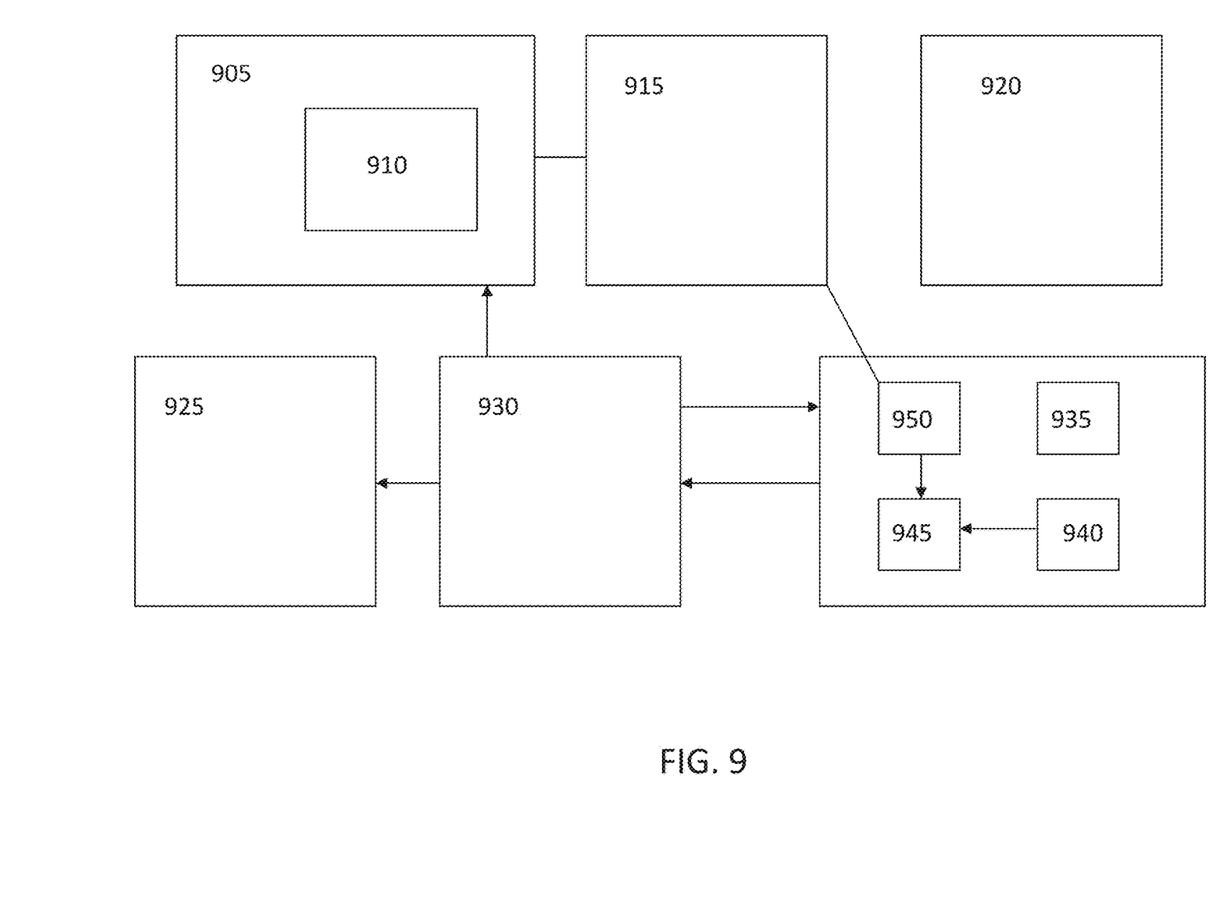
FIG. 9 illustrates an exemplary block diagram of a reader.

As visible in FIG. 9, in some embodiments the reader may comprise a transmission module (905) with an RF modulator (910) connected to a transceiver link board (915). In some embodiments, the transceiver link board may comprise a capacitor and inductor in parallel. The inductor can represent a coil or antenna and configured to communicate or transfer power with a corresponding implant (920). The implant may comprise an inductor in parallel with a capacitor, connected in series with a diode. The diode may connect to a capacitor in parallel with a resistor. The capacitor and inductor may be electrically connected with a transistor and a modulator. The signal processing may be carried out by a computer or cell phone (925). The interface processing may be a USB controller (930). The reader system may comprise an RF acquisition and mixing module (935), a filtering module (940), a demodulation module (945), and an RF front end processing module (945).

The readout system can be implemented using discrete components but the system could be expensive, difficult to maintain and bulky. Hence, implementation using minimal number of integrated components can be advantageous for having a small form-factor. Employing a small form-factor can also result in flexible readers which can be shaped in different forms and can conform to different contours for use in different applications. One example is using biocompatible flexible circuit board based systems to conform to body contours for easy readout.

Power can be transferred from the reader to the wireless device through near-field or far-field coupling. Near-field coupling occurs in close proximity though electromagnetic coupling while far-field coupling happens at distances larger than the wavelength employed, through electromagnetic radiation. The coupling or radiation can performed between two coils or antennas residing on the reader and on the wireless sensor. The coil or antenna can be designed on the same board as the reader electronics for better impedance matching and for easier integration. Alternatively, such structures can be made in special materials and later connected to the reader electronics. The same coil or antenna can be utilized for both powering and communication with the wireless sensor.

The powering and communication frequency, that is the operating frequency of the antenna or coil, is limited to FCC-designated bands. Different ISM frequency bands are available for these applications, which can be selected depending on the size of the wireless sensor. For instance, to achieve a small form factor, the UHF 900 MHz band is desirable, and it enables the use of existing RFID protocol and infrastructure to achieve low-cost and reliable performance.

Figure 10:
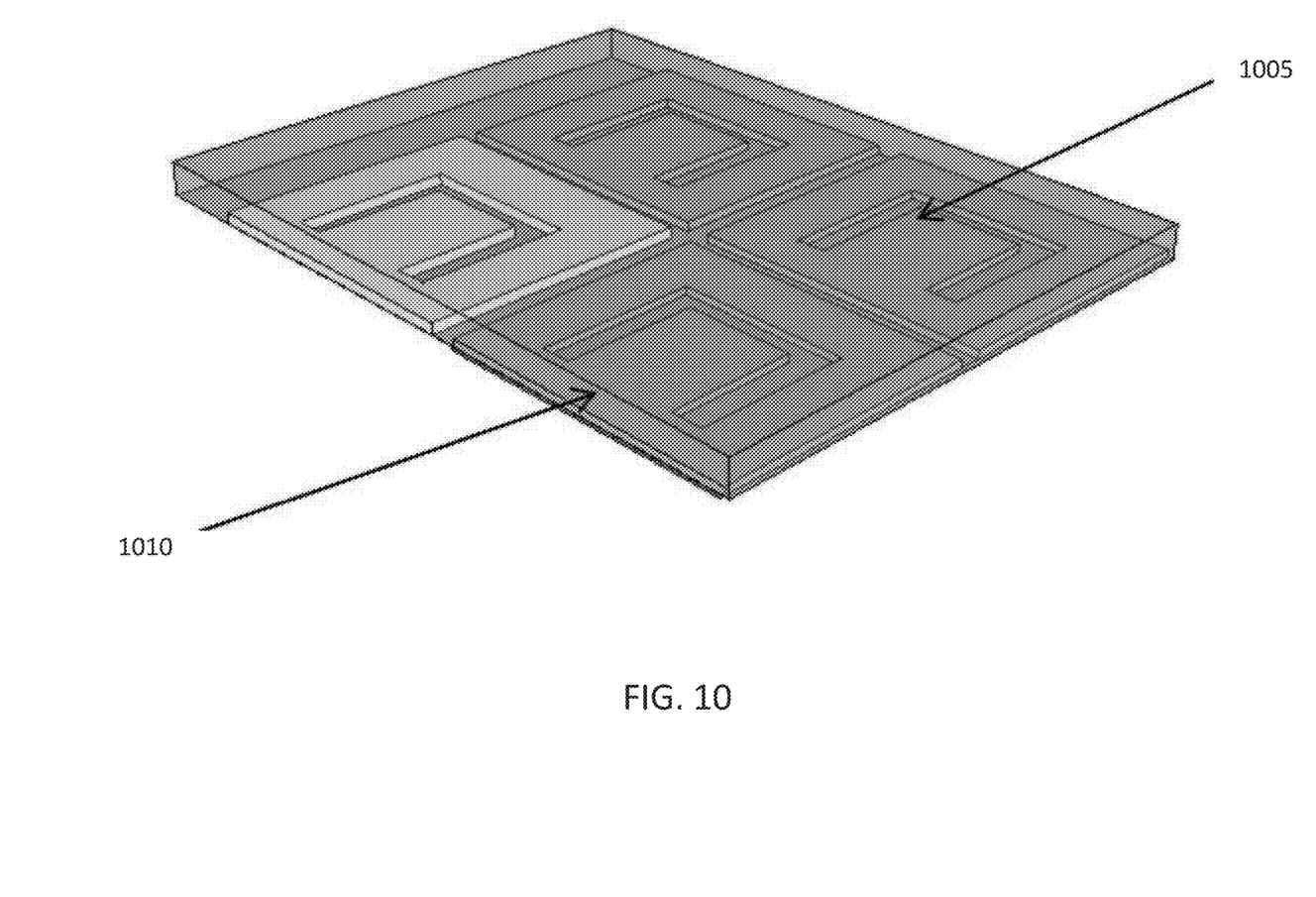
FIG. 10 illustrates an antenna array to improve readout alignment with the sensor.

Array-based techniques can be used to improve the alignment efficiency of the reader with the sensor platform. Increased efficiency can also help in locating the device within a narrow area. For example if the sensor is implanted, its location can be determined through the reader, and can later be used for extraction. An example of an array of RF coils or antennas is shown in FIG. 10. In FIG. 10, the reader electronics can be placed on top (1005) while the antenna array can be placed on the bottom layer (1010). Multiplexing can be used to allow the same electronics to drive the entire array.

The external device can be incorporated into a user-friendly device such as a watch or a cell phone. Readout systems can be integrated into these platforms for seamless connectivity without the need of any extra accessory.

For optical readouts, one possible method to implement it is to use the cell phone camera light as the energy source and the cell phone camera as the detector. In several embodiments, IR wavelengths are used in the sensing systems of the present disclosure. The optical signal in near IR wavelengths can be detected by several standard cell phone cameras. The light used in most phones is intense enough to allow operation of the sensing system, and can provide enough power to the on-chip photovoltaic power harvesting system.

In other embodiments, for optical readout, an accessory can be designed to go on top of the camera and the camera light. The accessory can filter out extreme UV signals to protect skin and the enzyme in the sensor. The accessory can also be used to filter out the remaining part of the light for better detector operation. An app can be designed which allows the user to continuously keep the light on and see the feedback in the actual image or video, until a good alignment is found with the incoming light. The app can track the alignment based upon a maximum received signal. The app can also give the user directions to move the readout platform in specific directions to improve the signal reception. The user can then record either an image or a video to read the sensor output. The sensor can be designed to send the data stream with a specific header which can be used to detect the start of the next data word from the sensor to render readout easy. Image or video processing can be done as part of the app to decode the data. Users can take multiple consecutive readings to decrease the possibility of error.

Similar techniques can be used for RF readout. The reader can pinpoint the device location based upon the received signal characteristics (e.g. power, known data stream, etc.).

Wireless technologies can be used to relay the information from the readout units to a more sophisticated device like a smart phone, a tablet or a computer. This can allow further data processing as well as data storage for longer durations. One example is the use of Bluetooth™ based technologies to wirelessly connect the readout unit to another unit (smart phone, tablet, etc.) for trend monitoring, alarms, etc. The data can also be securely communicated to other useful entities like health care associates or family, through the smart platforms.

Figure 11:
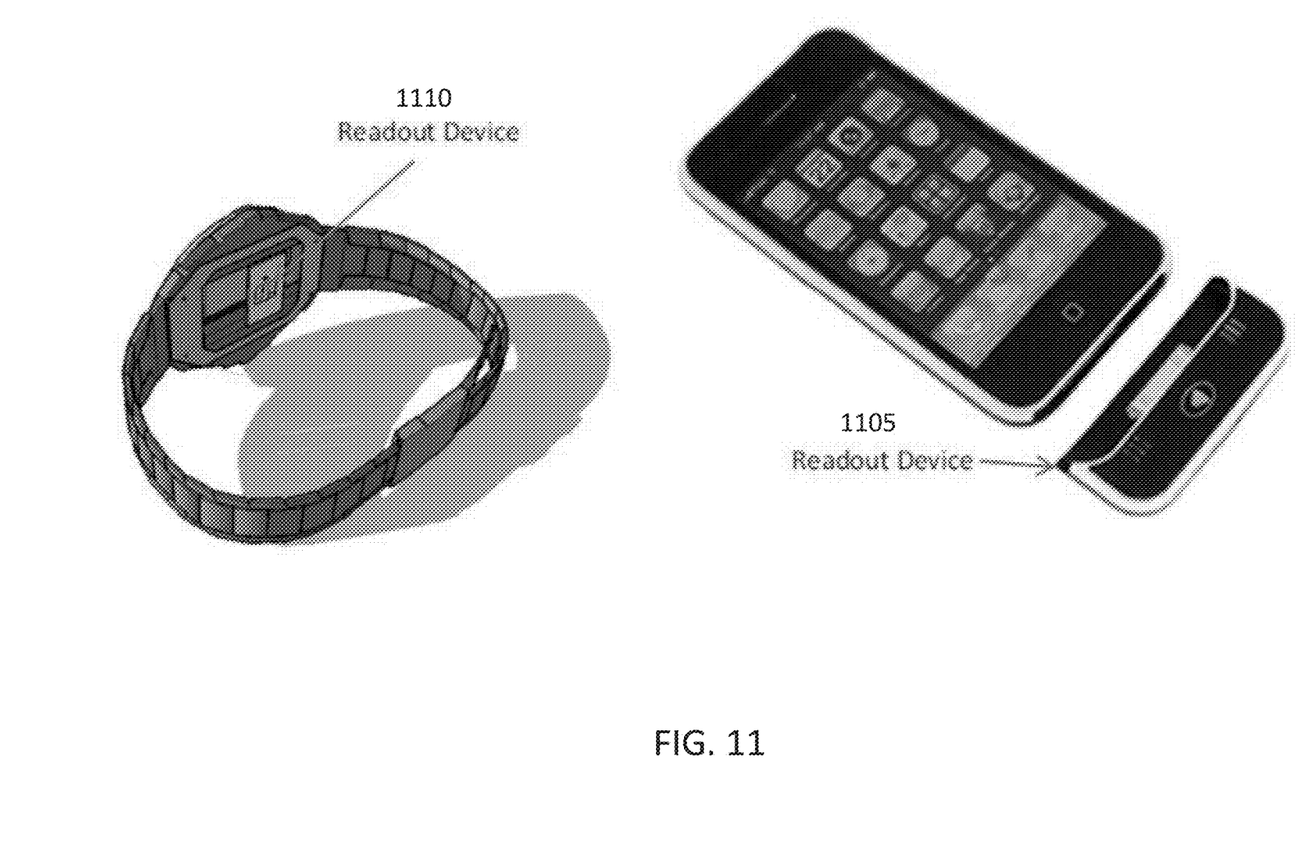
FIG. 11 illustrates readout devices integrated into user-friendly platforms.

FIG. 11 illustrates an exemplary readout device that can be attached to a smartphone (1105). Another readout device can be attached to a smartwatch (1110), for example to allow proximity with an implant on the skin.

Figure 12:
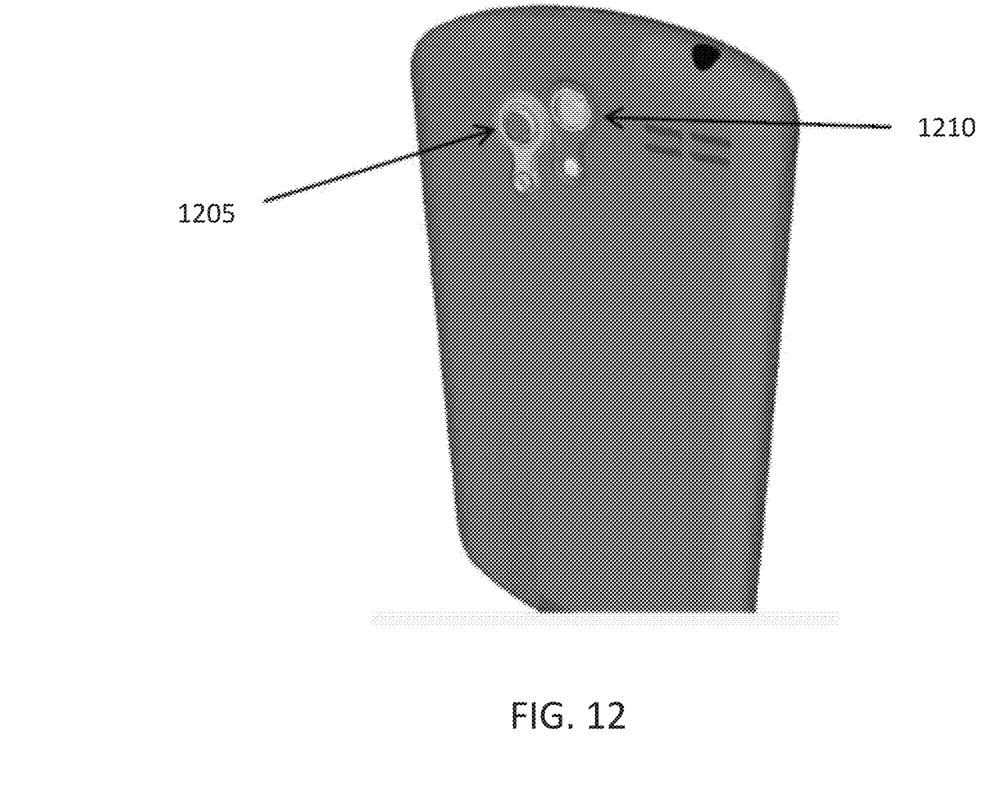
FIG. 12 illustrates an exemplary accessory designed as a snap-on module.

FIG. 12 illustrates an exemplary accessory designed as a snap-on module (1205) to be attached on the camera and camera light (1210). The module can have filters, for example UV filters. The smartphone can communicate with an implanted sensing device.

In some embodiments, the needles have a diameter less than 100, 10 or 1 micron. In other embodiments, the needles have a diameter less than 100 or 10 nm. In some embodiments, the wavelengths, for example IR wavelengths, are chosen so that it is transmitted through a body to which the sensing device is attached.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

What is claimed is:

1. A system comprising:
    a sensing device comprising:
        a substrate;
        a container on a top surface of the substrate;
        a plurality of needles on a bottom surface of the substrate, the plurality of needles connected to the container and configured to allow a fluid flow from needle tips to the container;
        at least one sensor on the substrate, the at least one sensor configured to analyze the fluid in the container; and
        an antenna or coil on the substrate; and
    a snap-on accessory, configured to attach on an external reader device, wherein:
        the external reader device comprises a camera and a camera light and is configured to communicate with the sensing device through the antenna or coil, and
        the snap-on accessory comprises filters, the filters configured to filter electromagnetic radiation from the camera light to the sensing device and from the sensing device to the camera.

2. The system of claim 1, wherein the substrate comprises an adhesive and is configured to attach to skin.

3. The system of claim 1, wherein each needle of the plurality of needles has a diameter less than 100 micrometer.

4. The system of claim 1, wherein each needle of the plurality of needles has a diameter less than 100 nanometer.

5. The system of claim 1, wherein the container contains a drug and the fluid flow is from the container to the needle tips.

6. The system of claim 1, wherein the container comprises a plurality of subcontainers, each subcontainer containing a drug different from other subcontainers.

7. The system of claim 1, further comprising an actuation module configured to actuate the fluid flow.

8. The system of claim 1, wherein the antenna or coil is further configured to receive power from the external reader device.

9. The system of claim 1, further comprising at least one photovoltaic cell on the substrate, the at least one photovoltaic cell configured to provide power to the at least one sensor.

10. The system of claim 1, wherein the substrate is silicon-on-insulator.

11. The system of claim 1, wherein the sensing device is configured to be implanted in a biological body.

12. The system of claim 1, wherein the at least one sensor comprises at least one first and second sensors, the first sensor configured to detect a signal different from the second sensor.

13. The system of claim 1, wherein the external reader device is a smartphone.

14. The system of claim 13, wherein the smartphone comprises an app configured to operate the sensing device and allow communication between the sensing device and the external reader device.

15. The system of claim 14, wherein the sensing device is configured to be implanted in a biological body and the app is further configured to detect a location of the implanted sensing device through the antenna or coil.

* * * * *